(12) United States Patent
Uhr et al.

(10) Patent No.: US 6,534,529 B2
(45) Date of Patent: *Mar. 18, 2003

(54) SYNERGISTIC INSECTICIDE MIXTURES

(75) Inventors: Hermann Uhr, Krefeld (DE);
Hans-Ulrich Buschhaus, Krefeld (DE);
Martin Kugler, Leichlingen (DE);
Franz Kunisch, Odenthal (DE);
Heinrich Schrage, Krefeld (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/091,896

(22) PCT Filed: Dec. 16, 1996

(86) PCT No.: PCT/EP96/05644

§ 371 (c)(1),
(2), (4) Date: Jun. 23, 1998

(87) PCT Pub. No.: WO97/24032

PCT Pub. Date: Jul. 10, 1997

(65) Prior Publication Data

US 2002/0006924 A1 Jan. 17, 2002

(30) Foreign Application Priority Data

Dec. 27, 1995 (DE) .......................... 195 48 872

(51) Int. Cl.$^7$ ................................ A61K 31/44
(52) U.S. Cl. ..................................... 514/341
(58) Field of Search ................... 514/341, 404

(56) References Cited

U.S. PATENT DOCUMENTS

| | | | |
|---|---|---|---|
| 4,531,002 A | 7/1985 | Harris .......................... 544/54 |
| 4,606,862 A | 8/1986 | Harris .................... 260/402.5 |
| 4,687,845 A | 8/1987 | Hollowood et al. .......... 544/54 |
| 4,742,060 A * | 5/1988 | Shiokawa et al. ........... 514/252 |
| 4,772,620 A | 9/1988 | Shiokawa et al. ........... 514/341 |
| 4,774,247 A | 9/1988 | Shiokawa et al. ........... 514/256 |
| 4,803,277 A | 2/1989 | Shiokawa et al. ........... 514/332 |
| 4,806,553 A | 2/1989 | Shiokawa et al. ........... 514/332 |
| 4,812,454 A | 3/1989 | Shiokawa et al. ........... 514/256 |
| 4,812,571 A | 3/1989 | Shiokawa et al. ........... 546/296 |
| 4,845,106 A | 7/1989 | Shiokawa et al. ........... 514/342 |
| 4,849,432 A | 7/1989 | Shiokawa et al. ........... 514/341 |
| 4,882,344 A | 11/1989 | Shiokawa et al. ........... 514/342 |
| 4,914,113 A | 4/1990 | Shiokawa et al. ........... 514/333 |
| 4,918,086 A | 4/1990 | Gsell .......................... 514/351 |
| 4,918,088 A | 4/1990 | Gsell .......................... 514/357 |
| 4,948,798 A | 8/1990 | Gsell .......................... 514/275 |
| 4,963,572 A | 10/1990 | Gsell .......................... 514/357 |
| 4,963,574 A | 10/1990 | Bachmann et al. .......... 514/357 |
| 4,988,712 A | 1/1991 | Shiokawa et al. ........... 514/340 |
| 5,001,138 A | 3/1991 | Shiokawa et al. ........... 514/342 |
| 5,032,589 A | 7/1991 | Shiokawa et al. ........... 514/245 |
| 5,034,404 A | 7/1991 | Uneme et al. .............. 514/365 |
| 5,034,524 A | 7/1991 | Shiokawa et al. ........... 544/124 |
| 5,039,686 A | 8/1991 | Davies et al. ................ 514/341 |
| 5,049,571 A | 9/1991 | Gsell .......................... 514/345 |
| 5,063,236 A | 11/1991 | Gsell .......................... 514/318 |
| 5,066,808 A | 11/1991 | Shiokawa et al. ....... 514/231.5 |
| 5,166,164 A | 11/1992 | Nanjo et al. ................. 514/357 |
| 5,204,360 A | 4/1993 | Shiokawa et al. ........... 514/342 |
| 5,232,940 A * | 8/1993 | Halton et al. ................ 514/407 |
| 5,256,679 A | 10/1993 | Minamida et al. .......... 514/357 |
| 5,280,123 A | 1/1994 | Nanjo et al. ................. 548/111 |
| 5,298,507 A | 3/1994 | Shiokawa et al. ........... 514/256 |
| 5,384,324 A | 1/1995 | Shiokawa et al. ........... 514/365 |
| 5,405,961 A | 4/1995 | Nanjo et al. ................. 544/243 |
| 5,428,032 A | 6/1995 | Shiokawa et al. ....... 514/226.8 |
| 5,461,167 A | 10/1995 | Shiokawa et al. ........... 548/202 |
| 5,580,889 A | 12/1996 | Shiokawa et al. ........... 514/343 |
| 5,719,146 A | 2/1998 | Shiokawa et al. ....... 514/229.2 |
| 5,750,704 A | 5/1998 | Shiokawa et al. ....... 546/275.1 |
| 5,952,358 A * | 9/1999 | Meunier et al. ............. 514/357 |
| 6,077,860 A * | 6/2000 | Meunier et al. ............. 514/341 |

FOREIGN PATENT DOCUMENTS

| | | |
|---|---|---|
| DE | 3639877 | 5/1988 |
| DE | 3712307 | 10/1988 |
| EP | 0295117 | * 12/1988 |
| EP | 0 428 941 | 5/1995 |
| EP | 0 375 907 | 1/1996 |
| JP | 63-287764 | 11/1988 |
| JP | 63-307857 | 12/1988 |
| JP | 2-207083 | 8/1990 |
| JP | 3-220176 | 9/1991 |
| JP | 3-246283 | 11/1991 |
| JP | 3-255072 | 11/1991 |
| JP | 3-279359 | 12/1991 |
| JP | 4-9371 | 1/1992 |
| WO | 91/04965 | 4/1991 |
| WO | 91/17659 | 11/1991 |
| WO | 9623411 | * 8/1996 |
| WO | 9637105 | * 11/1996 |

OTHER PUBLICATIONS

Worthing et al, "The Pesticide Manual", p. 491 9$^{th}$ Ed. (1991).*

* cited by examiner

Primary Examiner—Alton Pryor
(74) Attorney, Agent, or Firm—Richard E. L. Henderson; Raymond J. Harmuth

(57) ABSTRACT

The invention relates to insecticidal mixtures of fipronil and agonists or antagonists of nicotinic acetylcholine receptors for the protection of industrial materials and plants.

3 Claims, No Drawings

SYNERGISTIC INSECTICIDE MIXTURES

This Application is a 371 of PCT/EP96/05644 filed Dec. 16, 1999.

The invention relates to synergistic insecticidal mixtures of fipronil and agonists or antagonists of nicotinic acetylcholine receptors for the protection of industrial materials and as crop protection agents.

It is already known that fipronil can be employed for controlling wood-damaging animals (EP-295 117; U.S. Pat. No. 5,232,940). The very low vapour pressure of these compounds is an advantage.

However, relatively high concentrations are required when fipronil is used on its own. It is very difficult to deliver the concentrations required for activity sufficiently deep into the wood to be protected.

Furthermore, it is also known that agonists and antagonists of nicotinic acetylcholine receptors can be used for controlling insects and wood-damaging animals. Here, the active compound also has to be employed in relatively high concentrations to achieve an acute effect in the lower layers of the wood. In many instances, sub-lethal doses result in a change of the behaviour of the species, but in many cases these are reversible.

It has now been found that mixtures of fipronil and at least one agonist or antagonist of acetylcholine receptors of the formula (I) have synergistic activity and are suitable for protecting industrial materials, in particular wood, against attack by insects. These mixtures are also suitable in crop protection for controlling animal pests. Owing to this synergism, significantly lower amounts of active compounds can be used, i.e. the activity of the mixture is greater than the activity of the individual components.

The agonists and antagonists of the nicotinic acetylcholine receptors are known compounds, which are known from the following publications:

European Published Specifications Nos 464 830, 428 941, 425 978, 386 565, 383 091, 375 907, 364 844, 315 826, 259 738, 254 859, 235 725, 212 600, 192 060, 163 855, 154 178, 136 686, 303 570, 302 833, 306 696, 189 972, 455 000, 135 956, 471 372, 302 389;

German Offenlegungsschriften (German Published Specifications) Nos 3 639 877, 3 712 307;

Japanese Published Specifications Nos 03 220 176, 02 207 083, 63 307 857, 63 287 764, 03 246 283, 04 9371, 03 279 359, 03 255 072;

U.S. Pat. Nos. 5,034,524, 4,948,798, 4,918,086, 5,039,686, 5,034,404;

PCT Applications Nos WO 91/17 659, 91/4965;

French Application No. 2 611 114;

Brazilian Application No. 88 03 621.

The generic formulae and definitions described in these publications and the individual compounds described therein are expressly incorporated herein by reference.

Some of these compounds are summarized under the term nitromethylenes and related compounds.

Preferably, these compounds can be summarized under the general formula (I)

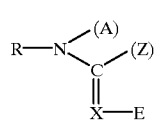

in which
R represents hydrogen, optionally substituted radicals acyl, alkyl, aryl, aralkyl, heteroaryl or heteroarylalkyl;

A represents a monofunctional group from the series hydrogen, acyl, alkyl, aryl or represents a bifunctional group which is linked to the radical Z;

E represents an electron-withdrawing radical;

X represents the radicals —CH= or =N—, where the radical —CH= may be linked to the radical Z instead of a H atom;

Z represents a monofunctional group from the series alkyl, —O—R, —S—R,

or represents a bifunctional group which is linked to the radical A. or the radical Particular preference is given to compounds of the formula (I) in which the radicals have the following meaning:

R represents hydrogen and represents optionally substituted radicals from the series acyl, alkyl, aryl, aralkyl, heteroaryl, heteroarylalkyl.

Examples of acyl radicals are formyl, alkylcarbonyl, arylcarbonyl, alkylsulphonyl, arylsulphonyl, (alkyl-)-(aryl-)-phosphoryl, which may themselves be substituted.

Examples of alkyl are $C_1$–$C_{10}$-alkyl, in particular $C_1$–$C_4$-alkyl, specifically methyl, ethyl, i-propyl, sec- or t-butyl, which may themselves be substituted.

Examples of aryl are phenyl, naphthyl, in particular phenyl.

Examples of aralkyl are phenylmethyl, phenethyl.

Examples of heteroaryl are heteroaryl having up to 10 ring atoms and N, O, S, in particular N, as hetero atoms. Specific examples are thiophenyl, furyl, thiazolyl, imidazolyl, pyridyl, benzothiazolyl.

Examples of heteroarylalkyl are heteroarylmethyl, heteroarylethyl having up to 6 ring atoms and N, O, S, in particular N, as hetero atoms.

Substituents which may be mentioned by way of example and by way of preference are:

alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propyloxy and n-, i- and t-butyloxy; alkylthio having preferably 1 to 4, in particular 1 or 2, carbon atoms, such as methylthio, ethylthio, n- and i-propylthio and n-, i- and t-butylthio; halogenoalkyl having preferably 1 to 4, in particular 1 or 2, carbon atoms and preferably 1 to 5, in particular 1 to 3, halogen atoms, the halogen atoms being identical or different, and preferred halogen atoms being fluorine, chlorine or bromine, in particular fluorine, such as trifluoromethyl, hydroxyl; halogen, preferably fluorine, chlorine, bromine and iodine, in particular fluorine, chlorine and bromine, cyano; nitro; amino; monoalkyl- and dialkylamino having preferably 1 to 4, in particular 1 or 2, carbon atoms per alkyl group, such as methylamino, methylethylamino, n- and i-propylamino and methyl-n-butylamino; carboxyl, carbalkoxy having preferably 2 to 4, in particular 2 or 3, carbon atoms, such as carbomethoxy and carboethoxy; sulpho (—$SO_3H$); alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl, and also heteroarylamino and heteroarylalkylamino such as chloropyridylamino and chloropyridylmethylamino.

A represents hydrogen and optionally substituted radicals from the series acyl, alkyl, aryl, which are preferably as defined above, A furthermore represents a bifunctional group. Examples include optionally substituted alkylene having 1 to 4, in particular 1 or 2, C atoms, examples of substituents being the substituents which have been mentioned further above.

A and Z together with the atoms to which they are attached may form a saturated or unsaturated heterocyclic ring. The heterocyclic ring may contain a further 1 or 2 identical or different hetero atoms and/or hetero groups. Preferred hetero atoms are oxygen, sulphur or nitrogen, and preferred hetero groups are N-alkyl, where the alkyl of the N-alkyl group contains preferably 1 to 4, in particular 1 or 2, carbon atoms. Examples of alkyl include methyl, ethyl, n- and i-propyl and n-, i- and t-butyl. The heterocyclic ring contains 5 to 7, preferably 5 or 6 ring members. Examples of the heterocyclic ring include pyrrolidine, piperidine, piperazine, hexamethylenimine, morpholine and N-methylpiperazine.

E represents an electron-withdrawing radical, specific examples being $NO_2$, CN, halogenoalkylcarbonyl such as 1,5-halogeno-$C_1$–$C_4$-carbonyl, in particular $COCF_2$.

X represents —CH= or —N=

Z represents optionally substituted radicals alkyl, —OR, —SR, —NRR, where R and the substituents are preferably as defined above.

Z, together with the atom to which it is attached and the radical

instead of X, may form a saturated or unsaturated heterocyclic ring. The heterocyclic ring may contain a further 1 or 2 identical or different hetero atoms and/or hetero groups. Preferred hetero atoms are oxygen, sulphur or nitrogen and preferred hetero groups are n-alkyl, where the alkyl or N-alkyl group contains preferably 1 to 4, preferably 1 or 2, carbon atoms. Examples of alkyl include methyl, ethyl, n- and i-propyl and n-, i- and t-butyl. The heterocyclic ring contains 5 to 7, preferably 5 or 6, ring members. Examples of the heterocyclic ring include pyrrolidine, piperidine, piperazine, hexamethyleneimine, morpholine and N-methylpiperazine.

The agonists and antagonists of the nicotinic acetylcholine receptors are preferably compounds of the formula (I) R represents

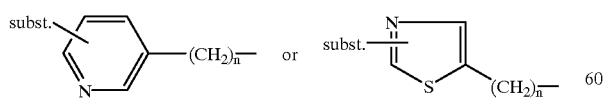

where
n represents 1 or 2,
Subst. represents one of the abovementioned substituents, especially halogen, in particular chlorine, and A, Z, X and E are each as defined above.

Specific examples are the following compounds:

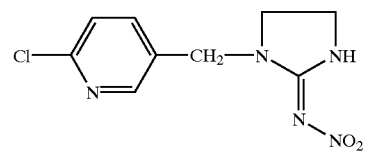

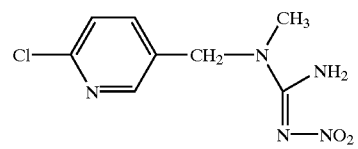

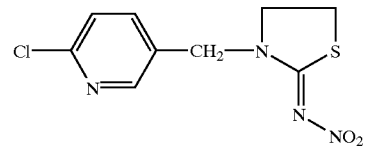

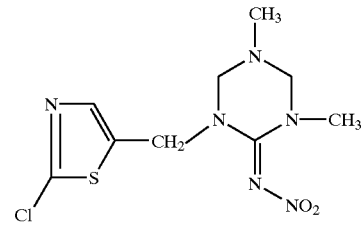

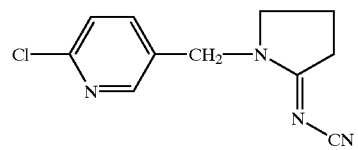

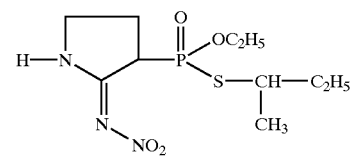

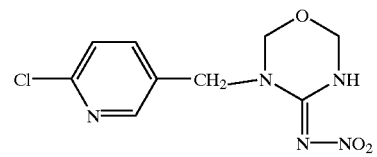

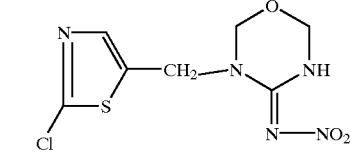

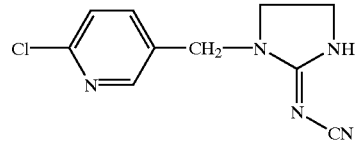

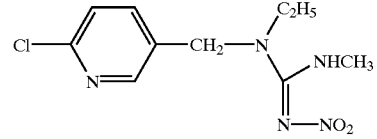

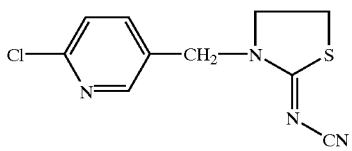
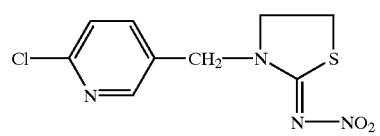
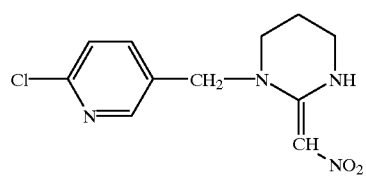
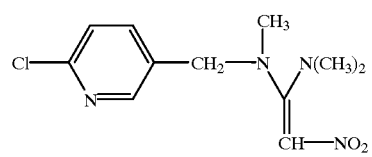
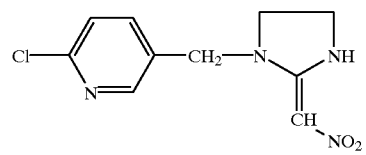
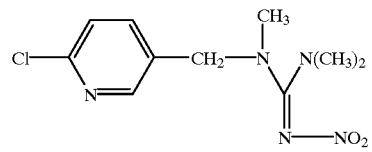
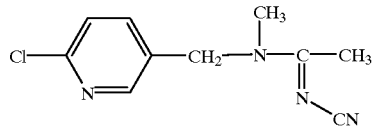
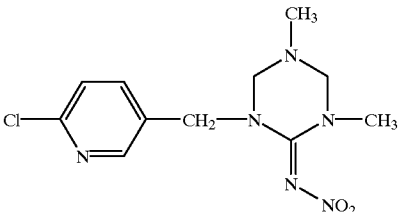
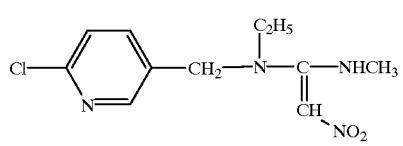
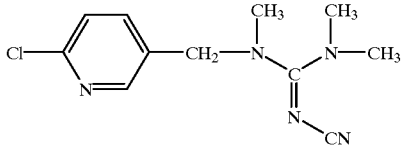
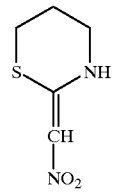
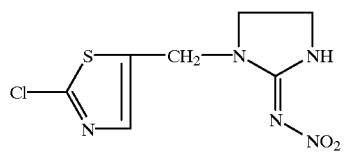
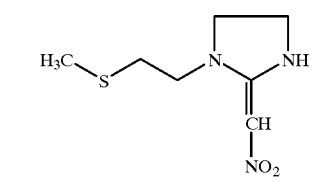
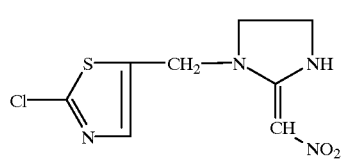
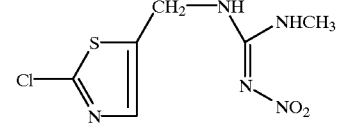
Very particularly preferred agonists and antagonists of the nicotinic acetylcholine receptors are compounds of the formulae below:
(IIa)
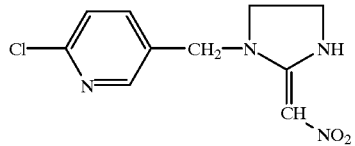
(IIb)
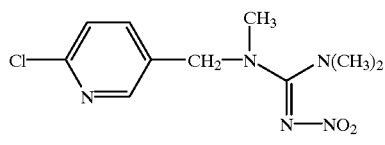
(IIc)
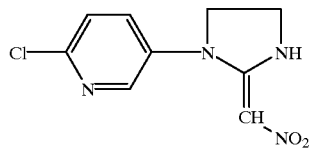
(IId)
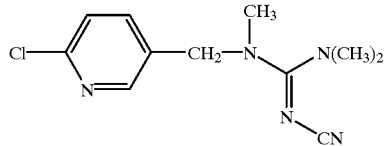

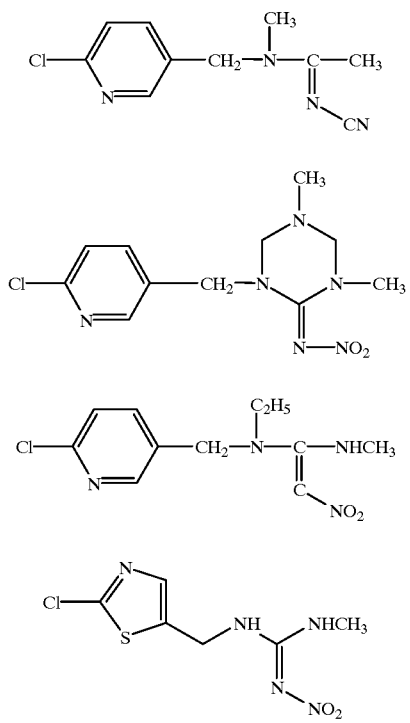

in particular the compound of the formula

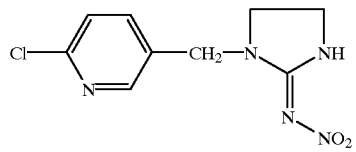

The active compound combination of fipronil and agonists and antagonists of nicotinic acetylcholine receptors of the formula (I) are very useful for protecting industrial materials, in particular wood, against attack by wood-destroying insects, such as, for example, 1. Beetles

*Hylotrupes bajulus, Chlorophorus pilosis, Anabium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec. Tryptodendron spec. *Apate monachus, Bostrychus capucins, Heterobostrychus bruneus,* Sinoxylon spec. *Dinoderus minutus*

2. Dermapterans

*Sirex juvencus, Urocerus gigas, Urocerus gigas* taignus, *Urocerus augur*

3. Termites

*Kalotermes flavicollis, Cryptotermes brevis, Heterotermes indicola, Reticulitermes flavipes, Reticulitermes santonensis, Reticulitermes lucilugus, Mastotermes darwiniensis, Zootermopsis nevadensis, Coptotermes formosanus.*

The ratio of the compounds of the formulae (I) employed and fipronil, and the total amount of the mixture, depends on the species and the occurrence of the insects. The optimum ratios and total application rates can be determined upon each use in each case by test series. In general, the ratio of the compounds of the general formulae (I) and fipronil is 1:100 to 100:1, preferably 1:10 to 10:1.

In general, the active compound combinations according to the invention can be incorporated into all compositions or formulations for the protection of wood, for example by mixing the active compounds with solvent or diluent, emulsifier, dispersant and/or binder or fixative, water repellent, if appropriate desiccants and UV stabilizers and, if appropriate, colorants and pigments and other processing auxiliaries, or as an additive to any other formulations for the protection of wood.

The solvent and/or diluent used is an organochemical solvent or solvent mixture and/or an oily or oil-type organochemical solvent or solvent mixture of low volatility and/or a polar organochemical solvent or solvent mixture and/or water and at least one emulsifier and/or wetting agent or consists thereof.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture or an aliphatic polar organochemical solvent or solvent mixture is replaced. Substances which are preferably used are aliphatic organochemical solvents having hydroxyl and/or ester and/or ether groups, such as, for example, glycol ether, esters and the like.

A particularly useful solvent/diluent is water, if appropriate as a mixture with one or more of the abovementioned organochemical solvents/diluents, emulsifiers and dispersants.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of the binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylene benzophenone, amines, such as, for example, alkanolamines, such as monoethanolamine or ammonia.

Wood which can be protected by the active compound mixture according to the invention or compositions comprising such a mixture are to be understood as meaning, for example: construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

Particularly effective protection of wood is achieved by large-scale industrial impregnation processes, for example vacuum, double-vacuum or pressure processes.

The insecticidal compositions or concentrates used for the protection of wood and timber products comprise the active compound combination in a concentration of 0.001 to 95% by weight, in particular 0.001 to 60% by weight.

Using the compositions according to the invention, it is possible to replace, in an advantageous manner, the insecticidal compositions which are currently available by more effective compositions. The compositions according to the invention exhibit good stability and have an advantageous broad insecticidal activity spectrum.

In ready-to-use applications, the mixtures according to the invention may also be present, if appropriate, as a mixture with other insecticides and, if appropriate, also with one or more fungicides in order to achieve additional activity against wood-destroying and wood-discoloring fungi. In many cases, additional synergisms are then observed.

Examples of insecticides which may optionally be admixed include:

phosphoric esters, such as azinphos-ethyl, azinphos-methyl, α-1(4-chlorophenyl)-4-(O-ethyl, S-propyl) phosphoryloxy-pyrazole, chlorpyrifos, coumaphos, demeton, demeton-S-methyl, diazinone, dichlorovos, dimethoate, ethoate, ethoprophos, etrimfos, fenitrothion, fenthion, heptenophas, parathion, parathion-methyl, phosalone, poxim, pirimiphos-ethyl, pirimiphos-methyl, profenofos, prothiofos, sulfprofos, triazophos and trichlorphon; carbamates, such as aldicarb, bendiocarb, α-2-(1-methylpropyl)-phenyl methylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb;

organosilicon compounds, preferably dimethyl(phenyl)silylmethyl 3-phenoxybenzyl ethers, such as dimethyl-(4-ethoxyphenyl)-silylmethyl 3-phenoxybenzyl ether or (dimethylphenyl)-silyl-methyl 2-phenoxy-6-pyridylmethyl ethers such as, for example, dimethyl-(9-ethoxy-phenyl)-silylmethyl 2-phenoxy-6-pyridylmethyl ether or [(phenyl)-3-(3-phenoxyphenyl)-propyl [(dimethyl)-silanes such as, for example, (4-ethoxyphenyl)-[3-(4-fluoro-3-phenoxyphenyl-propyl] dimethyl-silane, silafluofen;

pyrethroids, such as allethrin, alphamethrin, bioresmethrin, byfenthrin, cycloprothrin, cyfluthrin, decamethrin, cyhalothrin, cypermethrin, deltamethrin, alpha-cyano-3-phenyl-2-methylbenzyl 2,2-dimethyl-3-(2-chloro-2-trifluoro-methylvinyl)cyclopropanecarboxylate, fenpropathrin, fenfluthrin, fenvalerate, flucythrinate, flumethrin, fluvalinate, permethrin, resmethrin and tralomethrin;

nitroimines and nitromethylenes, such as 1-[(6-chloro-3-pyridinyl)-methyl]4,5-dihydro-N-nitro-1H-imidazol-2-amine (imidacloprid), N-[(6-chloro-3-pyridyl)methyl-] $N^2$-cyano-$N^1$-methylacetamide (NI-25);

abamectin, AC 303, 630, acephate, acrinathrin, alanycarb, aldoxycarb, aldrin, amitraz, azamethiphos, *Bacillus thuringiensis*, phosmet, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulfuryl fluoride, tar oils, teflubenzuron, tefluthrin, temephos, terbufos, tetrachlorvinphos, tetramethrin, O-tert-butyl-pyrimidin-5-yl-o-isopropyl-phosphorothiate, thiocyclam, thiofanox, thiometon, tralomethrin, triflumuron, trimethacarb, vamidothion, *Verticillium Lacanii*, XMC, xylylcarb, benfuracarb, bensultap, bifenthrin, bioallethrin, MERbioallethrin (S)-cyclopentenyl isomer, bromophos, bromophos-ethyl, buprofezin, cadusafos, calcium polysulphide, carbophenothion, cartap, quinomethionate, chlordane, chlorfenvinphos, chlorfluazuron, chlormephos, chloropicrin, chlorpyrifos, cyanophos, beta-cyfluthrin, alpha-cypermethrin, cyophenothrin, cyromazine, dazomet, DDT, demeton-S-methylsulphone, diafenthiuron, dialifos, dicrotophos, diflubenzuron, dinoseb, deoxabenzofos, diazacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramethylnon, hydrogen cyanide, hydroprene, IPSP, isazofos, isofenphos, isoprothiolane, isoxathion, iodofenphos, kadethrin, lindane, malathion, mecarbam, mephosfolan, mercurous, chloride, metam, Metarthizium, anisopliae, methacrifos, methamidophos, methidathion, methiocarb, methoprene, methoxychlor, methyl isothiocyanate, metholcarb, mevinphos, monocrotophos, naled, Neodiprion sertifer NPV, nicotine, omethoate, oxydemeton-methyl, pentachlorophenol, petroleum oils, phenothrin, phenthoate, phorate.

The other insecticides that may optionally be admixed may also be from the class of the compounds of the general formula (I).

Fungicides which may optionally be admixed are preferably:

Triazoles such as:

azaconazole, propiconazole, tebuconazole, cyproconazole, metconazole, amitrole, azocyclotin, BAS 480F, bitertanol, difenoconazole, fenbuconazole, fenchlorazole, fenethanil, fluquinconazole, flusilazole, flutriafol, imibenconazole, isozofos, myclobutanil, paclobutrazol, (±)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole and their metal salts and acid adducts.

Imidazoles such as:

imazalil, pefurazoate, prochloraz, triflumizole, 2-(1-tert-butyl)-1-(2-chlorophenyl)-3-(1,2,4-triazol-1-yl)-propan-2-ol, thiazolecarboxanilides such as 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one and their metal salts and acid adducts.

Methyl(E)-2-[2-[6-(2-cyanophenoxy)pyrimidin-4-yloxy]phenyl]3-methoxyacrylate, methyl(E)-2-[2-[6-(2-thioamidophenoxy)pyrimidin-4-yloxy]phenyl]-3-methoxyacrylate, methyl(E)-2-[2-[6-(2,6-difluorophenoxy)pyrimidin-4-yloxy]phenyl]-3-methoxyacrylate, methyl(E)-2-[2-[3-(pyrimidin-2-yloxy)phenoxy]phenyl]-3-methoxyacrylate, methyl(E)-2-[2-[3-(5-methylpyrimidin-2-yloxy)-phenoxy]phenyl]-3-methoxyacrylate, methyl(E)-2-[2-[3-(phenyl-sulphonyloxy)phenoxy]phenyl-3-methoxyacrylate, methyl(E)-2-[2-[3-(4-nitrophenoxy)phenoxy]phenyl]-3-methoxyacrylate, methyl(E)-2-[2-phenoxyphenyl]-3-methoxyacrylate, methyl(E)-2-[2-(3,5-dimethylbenzoyl)pyrrol-1-yl]-3-methoxyacrylate, methyl(E)-2-[2-(3-methoxyphenoxy)phenyl]-3-methoxyacrylate, methyl(E)-2[2-(2-phenylethen-1-yl)-phenyl]-3-methoxyacrylate, methyl(E)-2-[2-(3,5-dichlorophenoxy)pyridin-3-yl]-3-methoxy acrylate, methyl(E)-2-(2-(3-( 1,1,2,2-tetrafluoroethoxy) pheno xy)phenyl)-3-methoxyacrylate, methyl(E)-2-(2-[3-(alpha-hydroxybenzyl)phenoxy]phenyl)-3-methoxyacrylate, methyl(E)-2-(2-(4-phenoxy-pyridin-2-yloxy)phenyl)-3-methoxyacrylate, methyl(E)-2-[2-(3-n-propyloxyphenoxy)phenyl]3-methoxyacrylate, methyl(E)-2-[2-(3-isopropyloxyphenoxy)phenyl]-3-methoxyacrylate, methyl(E)-2-[2-[3-(2-fluorophenoxy)phenoxy]phenyl]-3-methoxyacrylate, methyl(E)-2-[2-(3-ethoxyphenoxy)phenyl]-3-methoxyacrylate, methyl(E)-2-[2-(4-tert-butyl-pyridin-2-yloxy)phenyl]-3-methoxyacrylate, methyl(E)-2-[2-[3-(3-cyanophenoxy)phenoxy]phenyl]-3-methoxyacry late, methyl(E)-2-[2-[(3-methyl-pyridin-2-yloxymethyl)phenyl]-3-methoxyacrylate, methyl(E)-2-[2-[6-(2-methylphenoxy)pyrimidin-4-yloxy]phenyl]-3-methoxyacrylate, methyl(E)-2-[2-(5-bromopyridin-2-yloxymethyl)phenyl]-3-methoxyacrylate, methyl(E)-2-[2-(3-(3-iodopyridin-2-yloxy)phenoxy)phenyl]-3-methoxyacrylate, methyl(E)-2-[2-[6-(2-chloropyridin-3-yloxy)pyrimidin-4-yloxy]phenyl]-3-methoxyacrylate, (E),(E)methyl-2-[2-(5,6-dimethylpyrazin-2-ylmethyloximinomethyl)phenyl]-3-methoxyacrylate, (E)-methyl-2-{2-[6-(6-methylpyridin-2-yloxy)pyrimidin-4-yloxy]phenyl}-3-methoxy-acrylate, (E),(E)methyl-2-{2-(3-methoxyphenyl)methyloximinomethyl]-phenyl}-3-methoxyacrylate, (E)methyl-2-{2-(6-(2-azidophenoxy)-pyrimidin-4yloxy]phenyl}-3-methoxyacrylate, (E), (E)methyl-2-{2-[6-phenylpyrimidin-4-yl)-methyloximinomethyl]phenyl}-3-methoxyacrylate, (E),(E)methyl-2-{2-[(4-chlorophenyl)-methyloximinomethyl]phenyl}-3-methoxyacrylate,(E)methyl-2-{2-[6-(2-n-propylphenyl)-1,3,5-triazin-4-yloxy]phenyl}-3-methoxyacrylate, (E), (E)methyl-2-{2-[(3-nitrophenyl)methyloximinomethyl]phenyl}-3-methoxyacrylate;

Succinate dehydrogenase inhibitors such as:
fenfuram, furcarbanil, cyclafluramid, furmecyclox, seedvax, metsulfovax, pyrocarbolid, oxycarboxin, shirlan, mebenil (mepronil), benodanil, flutolanil (Moncut);

naphthalene derivatives such as terbinafine, naftifine, butenafine, 3-chloro-7-(2-aza-2,7,7-trimethyl-oct-3-en-5-ine);

sulfenamides such as dichlofluanid, tolylfluanid, folpet, fluorfolpet; captan, captofol; benzimidazoles such as carbendazim, benomyl, furathiocarb, fuberidazole, thiophonatmethyl, thiabendazole or their salts;

morpholine derivatives such as fenpropimorph, falimorph, dimethomorph, dodemorph, aldimorph, fenpropidine and their arylsulphonates, such as, for example, p-toluenesulphonic acid and p-dodecylphenyl-sulphonic acid;

dithiocarbamates, cufraneb, ferbam, mancopper, mancozeb, maneb, metam, metiram, thiram zeneb, ziram:

benzothiazoles, such as 2-mercaptobenzothiazole;

benzamides, such as 2,6-dichloro-N-(4-trifluoromethylbenzyl)-benzamide;

boron compounds, such as boric acid, boric esters, borax;

formaldehyde and formaldehyde-releasing compounds, such as benzyl alcohol mono(poly)-hemiformal, oxazolidine, hexa-hydro-S-triazines, N-methylolchloroacetamide, paraformadehyde, nitropyrin, oxolinic acid, tecloftalam;

tris-N-(cyclohexyldiazeneiumdioxy)-aluminium, N-(cyclohexyldiazeniumdioxy)-tributyltin or K salts, bis-N-(cyclohexyldiazeniumdioxy)-copper, N-methylisothiazolin-3-one, 5-chloro-N-methylisothiazolin-3-one, 4,5-dichloro-N-octylisothiazolin-3-one, N-octyl-isothiazolin-3-one, 4,5-trimethylene-isothiazolinone, 4,5-benzoisothiazolinone, N-methylolchloroacetamide;

aldehydes, such as cinnamaldehyde, formaldehyde, glutaraldehyde, β-bromocinnamaldehyde;

thiocyanates, such as thiocyanatomethylthiobenzothiazole, methylenebisthiocyanate, and the like;

quaternary ammonium compounds, such as benzyldimethyltetradecylammonium chloride, benzyldimethyldodecylammonium chloride, didecyldimethaylammonium chloride;

iodine derivatives, such as diiodomethyl p-tolyl sulphone, 3-iodo-2-propinyl alcohol, 4-chlorophenyl-3- iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate;

phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol and their alkali metal and alkaline earth metal salts;

microbicides having an activated halogen group, such as chloroacetamide, bronopol, bronidox, tectamer, such as 2-bromo-2-nitro-1,3-propanediol, 2-bromo-4'-hydroxyacetophenone, 2,2-dibromo-3-nitrile-propionamide, 1,2-dibromo-2,4-dicyanobutane, β-bromo-β-nitrostyrene;

pyridines, such as 1-hydroxy-2-pyridinethione (and their Na, Fe, Mn, Zn salts), tetrachloro-4-methylsulphonylpyridine, pyrimethanol, mepanipyrim, dipyrithion, 1-hydroxy-4-methyl-6-(2,4,4-trimethylpentyl)-2(1H)-pyridine;

metal soaps, such as tin naphthenate, copper naphthenate, zinc naphthenate, tin octoate, copper octoate, zinc octoate, tin 2-ethylhexanoate, copper 2-ethylhexanoate, zinc 2-ethylhexanoate, tin oleate, copper oleate, zinc oleate, tin phosphate, copper phosphate, zinc phosphate, tin benzoate, copper benzoate and zinc benzoate;

metal salts, such as copper hydroxycarbonate, sodium dichromate, potassium dichromate, potassium chromate, copper sulphate, copper chloride, copper borate, zinc fluorosilicate, copper fluorosilicate, in particular mixtures with fixatives;

oxides, such as tributyltin oxide, $Cu_2O$, CuO, ZnO;

dialkyldithiocarbamates, such as Na and Zn salts of dialkyldithiocarbamates, tetramethylthiuram disulphide, potassium N-methyl-dithiocarbamate;

nitriles, such as 2,4,5,6-tetrachloroisophthalodinitrile, disodium cyanodithioimidocarbamate;

quinolines, such as 8-hydroxyquinoline, and their Cu salts;

mucochloric acid, 5-hydroxy-2(5H)-furanone;

4,5-dichlorodithiazolinone,4,5-benzodithiazolinone, 4,5-trimethylenedithiazolinone,4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, potassium N-hydroxymethyl-N'-methyldithiocarbamate, 2-oxo-2-(4-hydroxy-phenyl)acetohydroximic acid chloride, phenyl-(2-chloro-cyano-vinyl)sulphone, phenyl-( 1,2-dichloro-2-cyano-vinyl)sulphone;

Ag, Zn or Cu-containing zeolites, alone or enclosed in polymeric active compounds, or else mixtures of more than one of the abovementioned fungicides.

As already mentioned, the active compound mixtures are suitable for controlling animal pests, in particular insects, arachnids and nematodes, encountered in agriculture, in forests, in the protection of stored products, and in the hygiene field, and have good plant tolerance and favourable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria* migratorioides, *Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Euryga-ster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi, Phylloxera vastatrix,* Pemphigus spp., Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, Acarus siro, Argas spp., Ornithodoros spp., *Dermanyssus gallinae,* Eriophyes ribis, *Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The active compound mixtures according to the invention can be present in their commercially available formulations and in use forms prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia. Specific examples of mixing partners include the insecticides and fungicides mentioned further above.

The active compound content of the use forms prepared from the commercially available formulations can vary within wide limits. The active compound concentration of the use forms can be from 0.0000001 to 95% by weight of active compound, preferably between 0.0001 and 1% by weight.

The active compound mixtures can be converted into the customary formulations, such as solutions, emulsions, suspensions, powders, foams, pastes, granules, aerosols, active-compound-impregnated natural and synthetic materials, very fine encapsulations in polymeric substances and in coating compositions for seed, furthermore in formulations with smokes, such as fumigating cartridges, fumigating cans, fumigating coils and the like, and also ULV cold mist and warm mist formulations.

These formulations are prepared in a known manner, for example by mixing the active compounds with extenders, that is, liquid solvents, pressurized liquefied gases and/or solid carriers, optionally with the use of surfactants, that is, emulsifiers and/or dispersing agents, and/or foam-formers. If the extender used is water, it is also possible to use for example organic solvents as auxiliary solvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water; by liquefied gaseous extenders or carriers are meant liquids which are gaseous at ambient temperature and under atmospheric pressure, for example aerosol propellant, such as halogenated hydrocarbons and also butane, propane, nitrogen and carbon dioxide; suitable solid carriers are: for example, ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersing agents are: for example, lignin-sulphite waste liquors and methylcellulose.

Tackifiers such as carboxy-methylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 percent by weight of active compound composition, preferably between 0.5 and 90 percent by weight of active compound composition.

What is claimed is:

1. A method for the protection of wood against insecticidal attack comprising the step of applying a synergistically effective amount of fipronil and a compound of the formula (IIi)

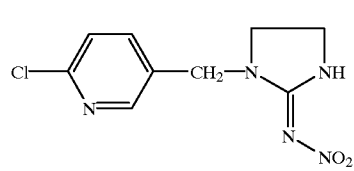

in a ratio of from 1:100 to 100:1 onto and/or into the wood to be protected.

2. The method of claim 1 wherein said fipronil and said compound of the formula (IIi) are impregnated into at feast a portion of said wood by an impregnation process selected from the group consisting of a vacuum, a double-vacuum and a pressure impregnation process.

3. The method of claim 2 wherein said fipronil and compound of the formula (IIi) comprise an active compound combination in a concentration of 0.001 to 95% by weight of an insecticidal composition for the protection of products selected from the group consisting of wood and timber products.

* * * * *